(12) United States Patent
Ning et al.

(10) Patent No.: US 11,480,510 B2
(45) Date of Patent: Oct. 25, 2022

(54) METHOD AND DEVICE FOR DYNAMICALLY MONITORING SUSPENDED MATTER BASED ON ANNULAR INTERLEAVING ARRAY

(71) Applicant: SOUTH CHINA UNIVERSITY OF TECHNOLOGY, Guangzhou (CN)

(72) Inventors: Gengxin Ning, Guangzhou (CN); Qiuyan Ning, Guangzhou (CN); Bowen Wang, Guangzhou (CN); Jun Zhang, Guangzhou (CN); Yizhi Feng, Guangzhou (CN); Fei Ji, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 791 days.

(21) Appl. No.: 16/463,392

(22) PCT Filed: Nov. 20, 2017

(86) PCT No.: PCT/CN2017/111892
§ 371 (c)(1),
(2) Date: May 23, 2019

(87) PCT Pub. No.: WO2018/233198
PCT Pub. Date: Dec. 27, 2018

(65) Prior Publication Data
US 2019/0353572 A1  Nov. 21, 2019

(30) Foreign Application Priority Data
Jun. 21, 2017  (CN) .......................... 201710474523.3

(51) Int. Cl.
*G01N 15/06* (2006.01)
*G01N 33/18* (2006.01)
*G01N 15/00* (2006.01)

(52) U.S. Cl.
CPC ......... *G01N 15/06* (2013.01); *G01N 33/1886* (2013.01); *G01N 2015/0053* (2013.01)

(58) Field of Classification Search
CPC ............... G01N 15/06; G01N 33/1886; G01N 2015/0053; G01N 2015/0687; G01N 15/02; G01P 5/241
See application file for complete search history.

(56) References Cited

U.S. PATENT DOCUMENTS

2008/0080314 A1 * 4/2008 Brumley ................. G01P 5/241
367/89

FOREIGN PATENT DOCUMENTS

CN    105738469    7/2016
CN    107144506    9/2017
(Continued)

*Primary Examiner* — David Z Huang
(74) *Attorney, Agent, or Firm* — JMB Davis Ben-David (57) ABSTRACT

Provided are a method and device for dynamically monitoring suspended matter based on an annular interleaving array. An annular multi-band interleaving array used thereby can be combined with the Doppler effect to on-line measure the concentration and linearity distribution of the suspended matter and a three-dimensional flow velocity of suspended water, thus realizing real-time monitoring of water quality. A frequency range needing to be measured is divided into different frequency bands, and different transceiving transducer arrays are used to transmit and receive measurement signals, so that the concentration and linearity distribution of various suspended matter with an extremely large linearity range can be obtained through one measurement.

10 Claims, 4 Drawing Sheets

(56) References Cited

FOREIGN PATENT DOCUMENTS

| | | |
|---|---|---|
| JP | 2010261719 | 11/2010 |
| WO | 2014002078 | 1/2014 |

* cited by examiner

METHOD AND DEVICE FOR DYNAMICALLY MONITORING SUSPENDED MATTER BASED ON ANNULAR INTERLEAVING ARRAY

CROSS-REFERENCE TO RELATED APPLICATIONS

This is the U.S. National Stage of International Patent Application No. PCT/CN2017/111892 filed Nov. 20, 2017, which was published in Chinese under PCT Article 21(2), and which in turn claims the benefit of Chinese Patent Application No. 201710474523.3 filed on Jun. 21, 2017.

TECHNICAL FIELD

The present invention relates to the field of dynamic monitoring of suspended matters in liquid, in particular to a method and a device for dynamically monitoring suspended matters based on an annular interleaving array.

BACKGROUND ART

Suspended matter concentration is an important factor affecting the quality of water and is also an important indicator for environmental monitoring. At the same time, the sedimentation of suspended matters also causes algae pollution. The detection of underwater suspended matter concentration and velocity, especially the detection of suspended matters with multi-scale resolution, is of great significance for the prevention and control of water pollution and the development of marine economy.

There are some measuring instruments and methods in the market for detecting suspended matters. Firstly, the gravimetric method measures the suspended matter concentration by sampling, filtering, drying, weighing and the like, which provides accurate measurement and simple operation, but the sampling and the measurement condition may affect the accuracy of the result, and data from just a few spots can hardly reflect the change and distribution of water quality in a wide range of waters. Secondly, the optical method measures the suspended matter concentration by the attenuation and scattering of light, but the commonly used optical instruments are elaborate and expensive, and the optical properties of light in water vary with the suspended matter concentration of the water, which limits the application of the optical method. Thirdly, the remote sensing technology quantitatively analyzes the spatial distribution and dynamics of large-area water conditions (including suspended matter content.) through satellites or aerial remote sensing information, and is available for macroscopic, large-area and periodic dynamic monitoring; however, the satellite remote sensing data needs to be verified with field data and a model should be constructed based on both satellite remote sensing data and field data, which also limits the application of real-time, convenient, efficient and widely used measurement of suspended matter concentration and size. As for measuring instrument, Jackson candle turbidity meter which is a standard turbidity meter can only be used to measure water samples having turbidity more than 25 degrees directly and is very inconvenient for use in low-turbidity water, and the measurement results vary with each individual. In addition, the above methods generally measure the concentration and size of suspended matters separately and do not take the motion of the suspended matters into consideration.

SUMMARY OF THE INVENTION

The main objective of the present invention is to overcome the defects of the prior art by providing a method for dynamically monitoring suspended matters based on an annular interleaving array, which uses different transceiving transducer arrays to send and receive signals, and can obtain the concentration and size distribution of various suspended matters in a large size range by one single measurement.

Another objective of the present invention is to provide a device for dynamically monitoring suspended matters based on the method.

The objectives of the present invention are realized through the following technical solutions:

A method for dynamically monitoring suspended matters based on an annular interleaving array, comprising the following steps:

S1 transmitting a signal;

wherein a measuring device is stationary relative to the ground and transmits the signal s(t) vertically downward in water containing suspended matters:

$$s(t) = A\frac{\sin(Wt)}{\pi t}\cos(2\pi f_0 t)$$

in the formula, A is the amplitude of the signal, W is the unilateral bandwidth of the signal, $f_0$ is the center frequency of the signal, and the power spectrum of the signal is a rectangular pulse having an amplitude of 0.5A, a bandwidth of 2W and a center frequency of $f_0$ on the positive axis:

$$S(f)=1/2A, f_0-W \leq f \leq f_0+W;$$

the signal is transmitted once every period T, i.e., the transmission frequency is F=1/T, and the transmission duration is $T_0$, $T_0$<T;

the frequency range of s(t) is within frequency ranges of used transmitting transducer and receiving transducers, and a reflector is arranged directly under each transmitting transducer to ensure that the receiving transducers can receive reflected signals sufficiently;

S2 calculating the frequency of the signal arriving at the reflector;

wherein a 3D Cartesian coordinate system is established using the ground as the reference frame, the position of an ultrasonic transmitting probe S as the coordinate origin and the direction perpendicularly downward to the ground as the z direction, such that the coordinates of S are (0,0,0), the coordinates of the reflector G are (0,0,z), and a plurality of the receiving transducers and the ultrasonic transmitting probe S are in the same plane;

the transmitting transducer S transmits the signal in the positive direction of the z axis, namely $\overrightarrow{SG}$ direction, with a frequency F, and the unit vector in the z direction is expressed as $\overrightarrow{1_{SG}}=(0,0,1)$; suppose the water velocity is $\overrightarrow{v_w}=(v_{wx}, v_{wy}, v_{wz})$, wherein $v_{wx}$, $v_{wy}$ and $v_{wz}$ respectively represent components of the water velocity on coordinate axes x, y and z, then the water velocity in the S→G direction is:

$$v_{w\_SG}=\overrightarrow{v_w}\cdot\overrightarrow{1_{SG}}=v_{wz}$$

with small volume and mass, the suspended matters have a flow velocity in water mainly related to the water velocity, so the estimation of sedimentation velocity or flow velocity of the suspended matters can be converted into the calculation of flow velocity of the water body with suspended matters; assume that the propagation velocity of sound wave in water is c, since the signal transmitting point S is stationary, according to the Doppler effect, the frequency of the signal arriving at the reflector is:

$$f_G = \frac{c + v_{wz}}{c} F;$$

S3 calculating the frequency of the signal arriving at a receiving probe;

L represents the distance of transmitting the signal from the transmitting transducer S to the reflector G and finally to a receiving transducer $R_i$, $\overrightarrow{GR_i}$ is the propagation direction of the signal transmitted from the reflector G to the receiving transducer $R_i$, $\alpha_i$, $\beta_i$ and $\gamma_i$ are respectively angles between the vector $\overrightarrow{GR_i}$ and the coordinate axes x, y and z; the unit vector of the vector $\overrightarrow{GR_i}$, $\overrightarrow{1_{GR_i}} = (\cos \alpha_i, \cos \beta_i, \cos \gamma_i)$, is thus obtained, and the water velocity in the G→$R_i$ direction is:

$$v_{w\_GR_i} = \overrightarrow{v_w} \cdot \overrightarrow{1_{GR_i}} = v_{wx} \cos \alpha_i + v_{wy} \cos \beta_i + v_{wz} \cos \gamma_i;$$

when the sound wave is propagated from the reflector G to the receiving point $R_i$, the signal is subject to the Doppler effect under the action of water flow; the signal s(t) is transmitted once every period T at the transmission terminal, and is subject to the Doppler shift due to the Doppler effect in the process of propagation in water, so the reflected signal $r_i(t)$ finally received by the receiving terminal $R_i$ has a period of $T_{R_i}$, and a receiving frequency of $f_{R_i} = 1/T_{R_i}$; since the receiving terminal does not move, the frequency of the signal arriving at the $i^{th}$ receiving transducer $R_i$ is:

$$f_{R_i} = \frac{c}{c + v_{w\_GR_i}} f_G;$$

after rearrangement, in a process from transmitting to receiving the signal s(t), the relationship between the receiving frequency and the transmitting frequency is:

$$f_{R_i} = \frac{c + v_{wx}}{c} \cdot \frac{c}{c + v_{w\_GR_i}} F$$
$$= \frac{c + v_{wx}}{c + v_{wx}\cos\alpha_i + v_{wy}\cos\beta_i + v_{wz}\cos\gamma_i} F$$
$$= (1 + \Delta_i) F$$

wherein $\Delta$ is a Doppler factor;

S4 providing M (M≥3) receiving transducers to list M equations shown above to obtain the three unknown numbers, thus obtaining a three-dimensional flow velocity of the water body with suspended matters, i.e., the velocity of the suspended matters;

S5 estimating the concentration and size distribution of the suspended matters;

wherein the process of estimating the concentration and size distribution of the suspended matters by signal power spectra is as follows:

S5-1 sampling;

since the signal s(t) is attenuated in water and affected by the Doppler effect, the signal sampled from $r_i(t)$ (i=1, 2, . . . , M) received by the $i^{th}$ receiving transducer $R_i$ is:

$$r_i(n) = B_i \frac{\sin[(1+\Delta_i)WnT_s]}{\pi(1+\Delta_i)nT_s} \cos[2\pi(1+\Delta_i)f_0 nT_s] + w_i(n)$$

wherein $B_i$ and $\Delta_i$ are respectively the amplitude and the Doppler factor of the received signal, $w_i(n)$ is signal noise, the sampling frequency is $f_s = 1/T_s$ ($f_s > 2f$ ($f_0+W$)), and $\Delta_i$ can be obtained from step S3;

S5-2 performing 2N point discrete Fourier transform on the autocorrelation function $R_i(n)$ of the received signal to obtain $$S_{R_i}(k) = \sum_{n=0}^{N-1} R_i(n) e^{-j\frac{2\pi}{N}nk}, 0 \le k \le N-1$$

S5-3 analyzing the signal of the transceiving array, wherein the system function of the transmitting transducer S is $H_1(f)$, the system functions of the receiving transducers are all $H_2(f)$, the receiving transducers in a same transceiving array have the same parameters, and the system functions $H_1(f)$ and $H_2(f)$ can be obtained by checking the corresponding transducer parameters;

the signal s(t) is transmitted after passing through the system $H_1(f)$, and the received signal $r_i(t)$ also passes through the system $H_2(f)$, so the signal power spectra before and after propagation in water are respectively $H_1(f)S(f)$ and $S_{R_i}(f)/H_2(f)$;

S5-4 from step S5-3, the discrete signal power spectrum of the signal at the corresponding frequency $f_s k/N$ of the receiving transducer $R_i$ is $$\frac{S_{R_i}(k)}{H_2(f_s k/N)},$$

and the discrete signal power spectrum of the signal at the corresponding frequency $f_s k/N$ of the transmitting transducer S is $$\frac{A}{2} H_1(f_s k/N),$$

then an attenuation parameter $Q_k$ is obtained:

$$Q_k = \frac{\sum_{i=1}^{3} \frac{S_{R_i}(k)}{H_2(f_s k/N)}}{\frac{A}{2} H_1(f_s k/N)}, k = 0, 1, \ldots, N-1;$$

which indicates the attenuation parameter of the signal before and after passing through the water body;

S5-5 for the signals received by M receiving transducers, superimposing discrete power spectra of corresponding intervals of the signals, and obtaining the concentration of the suspended matters according to the attenuation parameter $Q_k$ (k=0,1, . . . , N-1) and the transmission distance L, wherein each frequency $f_s k/N$ of the signal corresponds to the concentration of the suspended matters with a size of quarter-wavelength.

Preferably, a plurality of transmitting transducers are used; each transmitting transducer transmits signals of a different frequency range; if a wide frequency range to be measured is [$f_1$, $f_m$], the wide frequency band may be divided into N bands: [$f_1$, $f_2$], [$f_3$, $f_4$], . . . , [$f_{m-1}$, $f_m$], N transmitting transducers are used, where a first transducer transmits signal $s_1(t)$ in a frequency range [$f_1$, $f_2$], a second transducer transmits signal $s_2(t)$ in a frequency range [$f_3$, $f_4$], and so on; one transmitting transducer corresponds to one transceiving array, and steps S1-S5 are repeated for different transceiving arrays to estimate the concentration, size distribution and velocity of the suspended matters in the water body.

Specifically, different frequency bands are consecutive or separated by a certain interval, and transducers for receiving the signal should also have corresponding frequency bands.

a device for dynamically monitoring suspended matters based on the above method, comprising an operation module, a processing module, a transceiving module, an output module and a power supply, wherein the power supply supplies power to all the modules; the operation module is connected with the processing module, and the processing module is connected with the transceiving module and the output module respectively;

the transceiving module comprises a measuring frame, N reflectors and N transceiving arrays; the measuring frame is used for connecting and fixing the reflectors and different transceiving arrays; the transceiving arrays are separated by a certain distance; each transceiving array comprises a transmitting transducer and M (M≥3) receiving transducers, and signal transmitting or receiving surfaces of all the transducers are in the same horizontal plane; the receiving transducers in each transceiving array are connected to the transmitting transducer, distances between the receiving transducers and the transmitting transducer in the same transceiving array are the same, and frequencies of the transmitting and receiving transducers in the same transceiving array are matched; the reflectors are located directly under the different transceiving arrays, and reflecting surfaces of the N reflectors are in the same horizontal plane;

when an operator inputs corresponding parameters to the operation module, the processing module generates signals of respective bands according to the parameter, transfers the signals to the transmitting transducers of the transceiving arrays with corresponding frequency bands in the transceiving module for transmission, and controls transmission periods of the transmitting transducers; for the signals transmitted by the transmitting transducer in a transceiving array, the corresponding receiving transducer array receives the reflected signals and transfers the reflected signals to the processing module; the processing module calculates the concentration and size distribution of the suspended matters, and calculates the three-dimensional flow velocity of water body with the suspended matters according to the Doppler effect; finally the measured concentration and size distribution of the suspended matters and the flow velocity of the water body are transferred to the output module for output display.

Preferably, the amount N of the transceiving arrays depends on the application scenario and range of measurement.

Preferably, a crossarm of the measuring frame for fixing the reflectors can be adjusted up and down to modify the height thereof.

Preferably, the processing module comprises a digital processor, a digital to analog converter and an analog to digital converter.

Preferably, the reflectors are made of a material that facilitates signal reflection.

Preferably, the measuring frame is made of a corrosion-resistant hard material.

Preferably, the transceiving arrays are connected by a metal or plastic material.

Compared with the prior art, the present invention has the following advantages:

1. In this invention, the frequency range to be measured is divided into different frequency bands, signals are transmitted and received by different transceiving transducer arrays, and the concentration and size distribution of various suspended matters within an extremely large size range can be obtained by one single measurement.

2. The annular multi-band interleaving array makes use of the Doppler effect to measure on line concentration and size distribution of the suspended matters and the three-dimensional flow velocity of the water body with suspended matters to realize real-time monitoring of water quality.

3. The annular multi-band interleaving array used by the present invention can realize separation of signals of different frequency bands, and can effectively suppress the interference among the signals of different frequency bands.

4. The reflectors of the present invention are made of a material that facilitates signal transmission, so that the receiving transducers can receive sufficient reflected signals.

5. The components used by the device of the present invention are all readily available, and the device is cheaper and more feasible than the optical device used in the optical method.

DETAILED DESCRIPTION OF THE PREFERRED EMBODIMENT

The following further describes the present invention in detail in combination with the embodiments and the accompanying drawings, but the embodiments of the present invention are not limited thereto.

EXAMPLE 1

Sound waves are elastic waves, and have the characteristics of small loss and long propagation distance in water, so the method uses sound waves as signals for measurement. To measure suspended matters of multiple scales (different diameters) ranging from decimeters (seaweed, floating garbage, etc.) to millimeters or even micrometers (organic and inorganic debris, algae, fine sand, etc.) in offshore and estuary water, broadband ultrasound having a wavelength of 0.25 times of the scale of the suspended matters is theoretically required for detection (the detection frequency spans from 10 kHz to 10 Mkz or more). The frequency of the existing underwater acoustic transducer ranges from tens of hertz to several kilohertz, and can even reach tens of megahertz, but the frequency of one single transducer can hardly cover the scale of all suspended matters in a water body. Therefore, a plurality of signals of different frequency ranges are required, wherein each transmitting transducer transmits signals of a certain frequency range, and a plurality of underwater acoustic transducers are used to transmit and receive signals, which can be realized by combination of multiple underwater acoustic transducers with different bands, that is, the detection system is of a multi-transmitting multi-receiving array structure. In addition, if the three-dimensional flow velocity of the suspended matters is desired, a one-transmitting multi-receiving array structure is required.

Based on the above principle, the present embodiment provides an active underwater acoustic detection model based on an annular multi-band interleaving array and a three-dimensional flow velocity detection method for a water body with suspended matters based on Doppler effect.

The present embodiment uses a signal as shown in formula (1):

$$s(t) = A\frac{\sin(Wt)}{\pi t}\cos(2\pi f_0 t) \qquad (1)$$

in the formula, A is the amplitude of the signal, W is the unilateral bandwidth of the signal, $f_0$ is the center frequency of the signal, and the power spectrum of the signal is a rectangular pulse having an amplitude of 0.5A, a bandwidth of 2W and a center frequency of $f_0$ on the positive axis.

$$S(f)=1/2A, f_0-W<f<f_0+W \qquad (2)$$

Since one transmitting transducer can only transmit ultrasonic signals in a certain frequency range, a plurality of transmitting transducers are required. Each transmitting transducer transmits signals of a different frequency range. If the wide frequency range to be measured is $[f_1, f_m]$, the wide frequency band can be divided into N bands $[f_1, f_2], [f_3, f_4], \ldots, [f_{m-1}, f_m]$. If N transmitting transducers are used, transducer 1 transmits signals $s_1(t)$ in the frequency range $[f_1, f_2]$, transducer 2 transmits signals $s_2(t)$ in the frequency range $[f_3, f_4]$, and so on. These different frequency bands can be continuous or separated by certain intervals. For example, the frequencies $f_2$ and $f_3$ as divided above can be separated by a certain interval or $f_2=f_3$, and the transducer for receiving the signals should also have corresponding frequency band.

Next, the steps of the measurement method of the present embodiment are analyzed by taking one of the transmitting transducers as an example.

Step S1: transmitting a signal

The measuring device is stationary relative to the ground, and transmits a signal vertically downward in water containing suspended matters, i.e., s(t) in formula (1). The signal is transmitted every period T, i.e., the transmitting frequency is F=1/T, and the transmitting duration is $T_0$ ($T_0<T$). The frequency range of s(t) should be included in the frequency range of transmitting transducers and receiving transducers used, and a reflector is arranged directly under each transmitting transducer to ensure that the receiving transducers can receive reflected signals sufficiently.

Step S2: analyzing a signal transmitted from the transmitting transducer to the reflector This step analyzes a sound wave transmitted from the ultrasonic transmitting transducer to the underwater reflector, and calculates the frequency of the signal arriving at the reflector.

Figure 1:
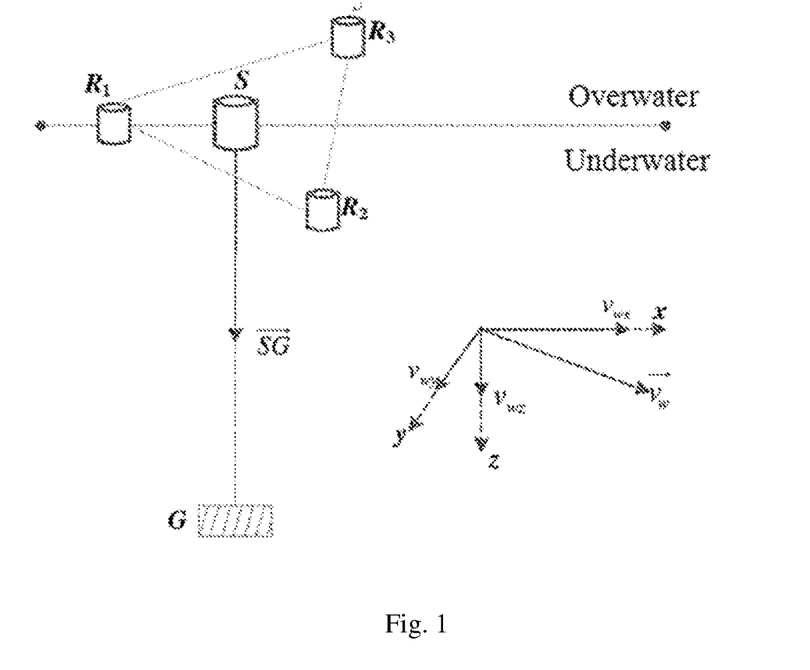
FIG. 1 is a schematic diagram of analyzing a signal transmitted from a transmitting transducer to an underwater reflector.

As shown in FIG. 1, a 3D Cartesian coordinate system is established using the ground as the reference frame, the position of an ultrasonic transmitting probe S as the coordinate origin and the downward direction perpendicular to the ground as the z direction, then the coordinates of S are (0,0,0), the coordinates of the reflector G are (0,0,z), and the corresponding three receiving transducers $R_1$, $R_2$ and $R_3$ and the ultrasonic transmitting probe S are in the same plane. It can be seen from step S1 that the transmitting transducer S transmits the signal to the positive direction of the z axis, i.e., $\overrightarrow{SG}$ in FIG. 1, the transmitting frequency is F, and the unit vector in the z direction can be expressed as $\overrightarrow{l_{SG}}=(0,0,1)$.

Suppose the water velocity is $\overrightarrow{v_w}=(v_{wx}, v_{wy}, v_{wz})$, wherein $v_{wx}$, $v_{wy}$ and $v_{wz}$ represent the components of the water velocity on the coordinate axes x, y and z respectively, then the water velocity in the S→G direction is $$v_{w\_SG}=\overrightarrow{v_w}\cdot\overrightarrow{l_{SG}}=v_{wz} \qquad (3)$$

with small volume and mass, the suspended matters have a flow velocity in water mainly related to the water velocity, so the estimation of sedimentation velocity or flow velocity of the suspended matters can be converted into the calculation of flow velocity of the water body with suspended matters; assume that the propagation velocity of sound wave in water is c, since the signal transmitting point S is stationary, according to the Doppler effect, the frequency of the signal arriving at the reflector is:

$$f_G = \frac{c + v_{wz}}{c}F \qquad (4)$$

Step S3: analyzing a signal transmitted from the reflector to the receiving transducer array This step analyzes a signal transmitted from the reflector to the receiving transducer array, and calculates the frequency of the signal arriving at the receiving probe.

Figure 2:
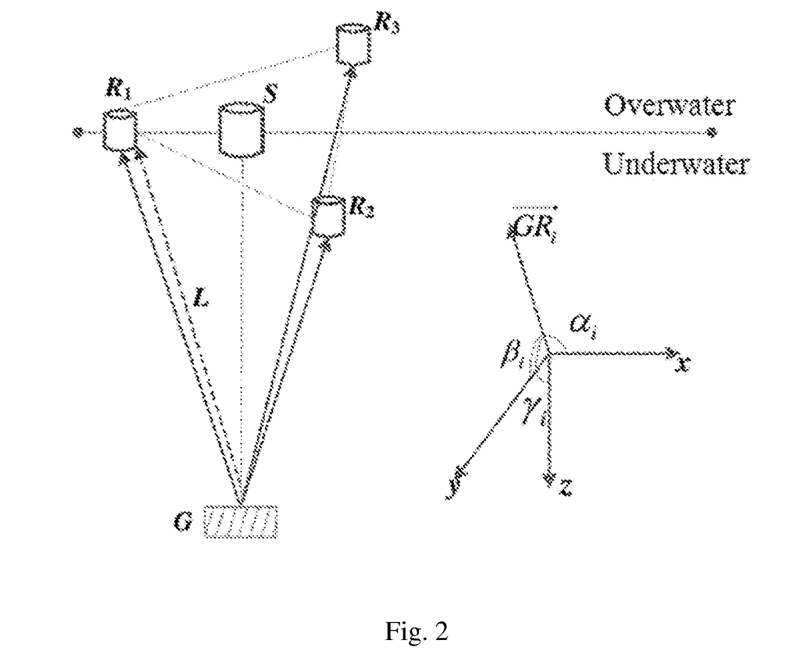
FIG. 2 is a schematic diagram of analyzing a signal transmitted from a reflector to a receiving transducer array.

FIG. 2 shows a receiving process, wherein the three receiving transducers $R_1$, $R_2$, $R_3$ are equidistant from the transmitting transducer S, L represents the distance of transmitting the signal from the transmitting transducer S to the reflector G and finally to a receiving transducer $R_i$, $\overrightarrow{GR_i}$ is the propagation direction of the signal transmitted from the reflector G to the receiving transducer $R_i$, $\alpha_i$, $\beta_i$ and $\gamma_i$ are respectively angles between the vector $\overrightarrow{GR_i}$ and the coordinate axes x, y and z; the unit vector of the vector $\overrightarrow{GR_i}$, $\overrightarrow{l_{GR_i}}=(\cos \alpha_i, \cos \beta_i, \cos y_i)$, is thus obtained, and the water velocity in the G→$R_i$ direction is:

$$v_{w\_GR_i}=\overrightarrow{v_w}\cdot\overrightarrow{l_{GR_i}}=v_{wx}\cos \alpha_i+v_{wy}\cos \beta_i+v_{wz}\cos \gamma_i \qquad (5)$$

when the sound wave is propagated from the reflector G to the receiving point $R_i$, the signal is subject to the Doppler effect under the action of water flow; the signal s(t) is transmitted once every period T at the transmission terminal, and is subject to the Doppler shift due to the Doppler effect in the process of propagation in water, so the reflected signal $r_i(t)$ finally received by the receiving terminal $R_i$ has a period of $T_{R_i}$, and a receiving frequency of $f_{R_i}=1/T_{R_i}$; since the receiving terminal does not move, the frequency of the signal arriving at the $i^{th}$ receiving transducer $R_i$ is:

$$f_{R_i} = \frac{c}{c+v_{w\_GR_i}} f_G \qquad (6)$$

after rearrangement, in a process from transmitting to receiving the signal s(t), the relationship between the receiving frequency and the transmitting frequency is:

$$f_{R_i} = \frac{c+v_{wx}}{c} \cdot \frac{c}{c+v_{w\_GR_i}} F \qquad (7)$$
$$= \frac{c+v_{wx}}{c+v_{wx}\cos\alpha_i + v_{wy}\cos\beta_i + v_{wz}\cos\gamma_i} F, \; i=1,2,3$$
$$= (1+\Delta_i)F$$

wherein $\Delta$ is a Doppler factor. Formula (7) contains three unknown numbers $v_{wx}$, $v_{wy}$ and $v_{wz}$, so three or more receiving transducers are required to list three or more equations as shown in the above formula, then the three unknown numbers can be obtained (if more than three equations are listed, three non-linear equations are selected from the equations to solve the three unknown numbers), and the obtained three-dimensional flow velocity of the suspended water body is the velocity of the suspended matters. In the present embodiment, three receiving transducers match with one transmitting transducer to form a transceiving array, for example, (S, $R_1$, $R_2$, $R_3$) in FIG. 1 and FIG. 2 constitute a transceiving array.

In the present embodiment, each receiving transducer in the same transceiving array is equidistant from the transmitting transducer, so in the same transceiving array, the transmission distance of the signal from the transmitting transducer S to the reflector G and finally to each receiving transducer is L.

Step S4: estimating the concentration and size distribution of the suspended matters It can be seen from step S3 that three or more receiving transducers are required for receiving one signal. In the present example, three receiving transducers $R_1$, $R_2$ and $R_3$ are used. Since the signal is affected by the action of suspended matters in water and the water body as well as Doppler effect, the signals received by the receiving terminals are different in frequency domain. For the transmitted signals s(t), the power spectra may also be different due to the influence of the transmitting transducer or other devices. Therefore, for the transceiving array, the process of estimating the concentration and size distribution of the suspended matters by using signal power spectra is as follows:

I. sampling. Since the signal s(t) is attenuated in water and affected by the Doppler effect, the signal sampled from $r_i(t)$ (i=1, 2, . . . , M) received by the $i^{th}$ receiving transducer $R_i$ is:

$$r_i(n) = B_i \frac{\sin[(1+\Delta_i)WnT_s]}{\pi(1+\Delta_i)nT_s}\cos[2\pi(1+\Delta_i)f_0nT_s] + w_i(n) \qquad (8)$$

wherein $B_i$ and $\Delta_i$ are respectively the amplitude and the Doppler factor of the received signal, $w_i(n)$ is signal noise, the sampling frequency is $f_s=1/T_s$ ($f_s>2f$ ($f_0+W$)), and $\Delta_i$ can be obtained from formula (7).

II. Performing 2N point discrete Fourier transform(DFT) on the autocorrelation function $R_i(n)$ of the received signal $r_i(n)$ to obtain $$S_{R_i}(k) = \sum_{n=0}^{N-1} R_i(n) e^{-j\frac{2\pi}{N}nk}, \; 0 \le k \le N-1$$

Figure 3:
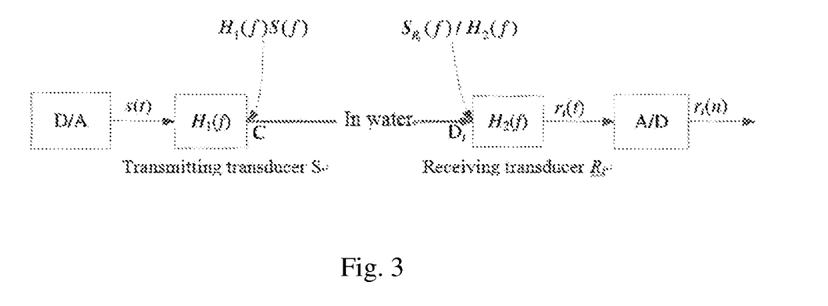
FIG. 3 is a schematic diagram showing states of the transceived signal.

III. Analyzing the signal of the transceiving array, such as spot C and D in FIG. 3 (i=1, 2 or 3). The system function of the transmitting transducer S is $H_1(f)$, the system functions of the receiving transducers are all $H_2(f)$, that is, the receiving transducers in a same transceiving array have the same parameters, and the system functions $H_1(f)$ and $H_2(f)$ can be obtained by checking the corresponding transducer parameters. As shown in the figure, the signal s(t) is transmitted after passing through the system $H_1(f)$, and the received signal $r_i(t)$ also passes through the system $H_2(f)$, so the signal power spectra before and after propagation in water are respectively $H_1(f)S(f)$ and $S_{R_i}(f)/H_2(f)$ ;

IV. from III, the discrete signal power spectrum of the signal at the corresponding frequency $f_s k/N$ of spot $D_i$ is $$\frac{S_{R_i}(k)}{H_2(f_s k/N)},$$

and the discrete signal power spectrum of the signal at the corresponding frequency $f_s k/N$ of spot C is $$\frac{A}{2}H_1(f_s k/N),$$

then an attenuation parameter $Q_k$ is obtained:

$$Q_k = \frac{\sum_{i=1}^{3} \frac{S_{R_i}(k)}{H_2(f_s k/N)}}{\frac{A}{2}H_1(f_s k/N)}, \; k=0,1,\ldots,N-1 \qquad (10)$$

which indicates the attenuation parameter of the signal before and after passing through the water body, i.e., spot C and $D_i$ in FIG. 3;

V. for the signals received by 3 receiving transducers, superimposing discrete power spectra of corresponding intervals of the signals, and obtaining the concentration of the suspended matters according to the attenuation parameter $Q_k$ (k=0,1, . . . , N-1), the transmission distance L and existing methods or formulas, wherein each frequency $f_s k/N$ of the signal corresponds to the concentration of the suspended matters with a size of quarter-wavelength.

Step S5: repeating the above steps for other transceiving arrays to estimate the concentration and size of the suspended matters.

The analysis on the power spectra in step S4 is on the positive axis and is performed on one transmitting transducer and three corresponding receiving transducers in one single transceiving array, and the analyses on the transceiving arrays of other frequency bands are identical. A plurality of transceiving arrays constitute an interleaving array, and the concentration, size distribution and velocity of the suspended matters in water body can be estimated by transceiving signals of multiple frequency bands according to steps S1~4, analyzing the power spectra before and after the signals pass through the water body, the Doppler effect, etc..

The above method uses an active acoustic detection model of an annular multi-band interleaving array to combine transmitting and receiving with an annular transceiving array which is constituted by one transmitting transducer and three or more receiving transducers of the same frequency band, thereby suppressing the interference among the transducers of different frequency bands. The concentration and size of the suspended matters in the liquid can be estimated by using a plurality of transceiving arrays covering different frequency bands according to the power and center frequency of the transmitted and received signals. In addition, the above method makes use of the Doppler effect by periodically transmitting the signals through the annular multi-band interleaving array, and analyzing the Doppler frequency shift of the signals, thereby realizing measurement of the three-dimensional flow velocity of the suspended water body, and finally realizing the dynamic monitoring of the liquid suspended matters.

Application example: for suspended matters in a range of (1.5 cm, 2 cm), the propagation velocity c of sound in water is about 1500 m/s, so the required measurement frequency range is about [300 KHz, 400 KHz], and the frequency range of the single transceiving array covering such range should include this range. The received signals are sampled, and the number of samples is N=200, that is, there are 200 parameters ($Q_0 \sim Q_{199}$). According to the estimation method in the above method, the concentration of suspended matters of two size can be estimated by using the parameters ($Q_0 \sim Q_{99}$) and the parameters ($Q_{100} \sim Q_{199}$).

EXAMPLE 2

Figure 4:
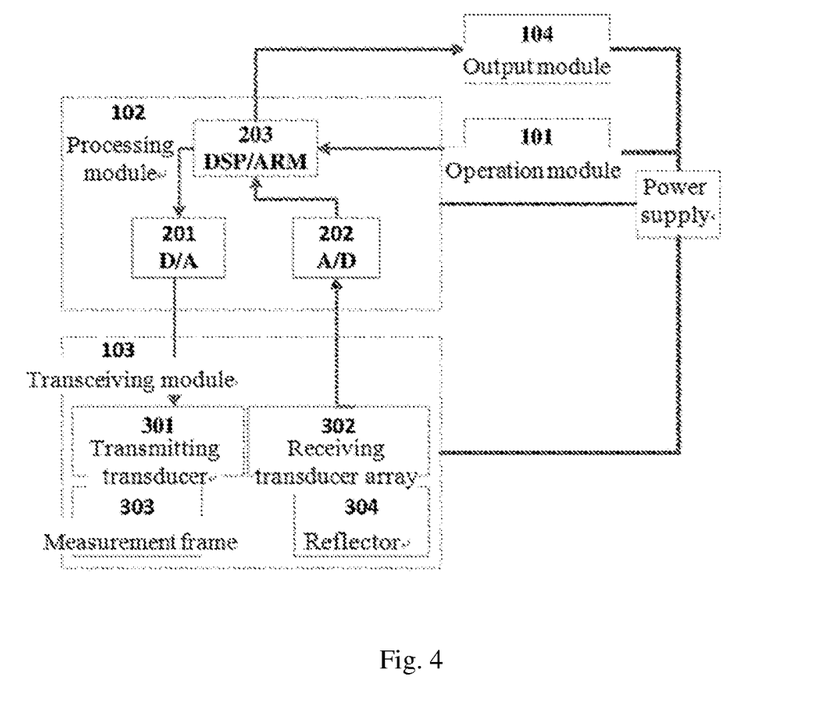
FIG. 4 is a schematic diagram of the components and connection of the modules of the device.

A measuring device based on the method in Embodiment 1 comprises an operation module 101, a processing module 102, a transceiving module 103, an output module 104 and a power supply, as shown in FIG. 4.

The operation module is connected with the processing module, and is mainly configured to perform man-machine interaction, wherein selection of the following parameters may be done according to the application scenario: the transmitting power, the frequency range transmitted or received by each transducer, and the frequency, amplitude and transmitting period of the signals of corresponding frequency bands.

The processing module is connected with the transceiving module and the output module respectively, which processes data according to the instruction input by the operation module, transmits and receives the waveform and data of the signals through the transceiving module, analyzes and processes the received signal data to obtain the measurement results of the concentration and size distribution of suspended matters and the flow velocity of a water body with suspended matters, and transmits the results to the output module for output display. The processing module includes a digital processor 203, a digital to analog converter 201 and an analog to digital converter 202. The digital processor 203 can be implemented with a DSP chip or an ARM, and the digital to analog converter (D/A) 201 and the analog to digital converter (A/D) 202 can also be implemented with DSP chips. The digital processor generates signals of respective bands according to the instruction of the operation module and transmits the same to the digital to analog converter 201. In addition, the digital processor acquires data of the received signals from the analog to digital converter 202 to estimate the concentration and size distribution of the suspended matters and estimate the flow velocity, and then transmits the estimated results to the output module for output. The digital to analog converter and the analog to digital converter serve as bridges between the digital processor and the transceiving module by performing digital to analog conversion on the signals generated by the digital processor and then transmitting the same to an interleaving array, performing analog to digital conversion on the signals received from the transceiving module and then transmitting the same to the digital processor for processing.

Figure 5:
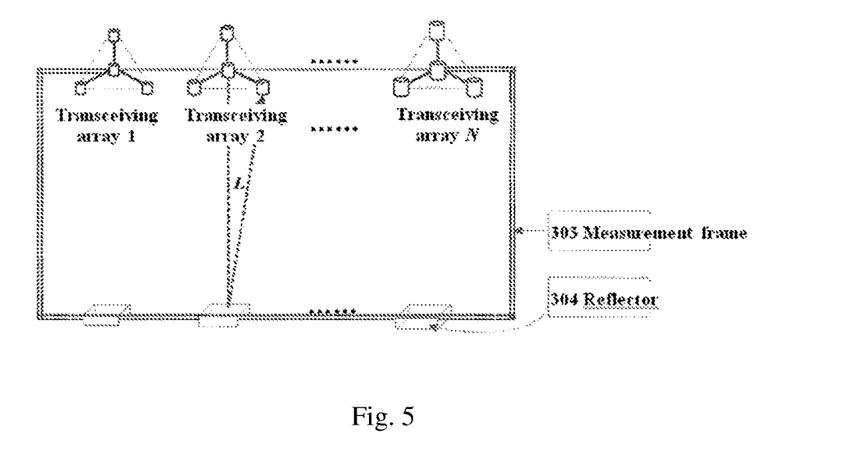
FIG. 5 is a schematic diagram of a specific structure of a transceiving module of the device.

The transceiving module 103 includes a measuring frame 303, reflectors 304 and N annular transceiving arrays (interleaving arrays). The amount N of the annular transceiving arrays depends on the application scenario and the range of measurement. The measuring frame 303 is used for connecting and fixing the reflectors 304 and the different transceiving arrays in the transceiving module 103. As shown in FIG. 5, the transceiving arrays are separated by certain distances $d_i$ (i=1,2, . . . , N-1), the distances $d_i$ may be unequal, and the transceiving arrays are connected and fixed by a metal or plastic material for transmitting and receiving signals of different frequency bands.

Figure 6:
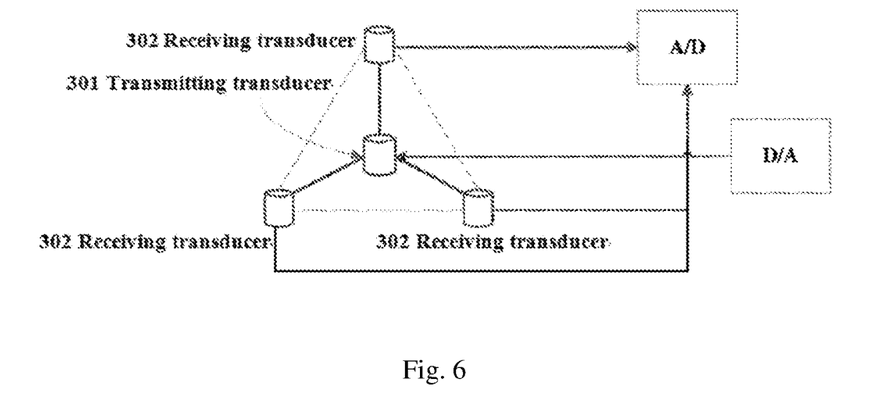
FIG. 6 is a structural diagram of an annular transceiving array.

Each transceiving array includes one transmitting transducer 301 and three (or three or above) receiving transducers 302. As shown in FIG. 6, the receiving transducers 302 in each transceiving array are connected to the transmitting transducer 301. The signal transmitting or receiving surfaces of the transmitting transducers 301 and the receiving transducers 302 of all the transceiving arrays are in the same horizontal plane, that is, the sizes of the transducers used in different transceiving arrays may be different, but the signal transmitting or receiving surfaces of all the transducers are located in the same horizontal plane. The transmitting transducer 301 transmits signals of different frequency bands which may be continuous or separated by a certain frequency, and the receiving transducers 302 receive the signals transmitted by the transmitting transducer 301 in the corresponding transceiving array. The transmitting and receiving transducers in the same transceiving array have matching frequencies, and are configured to acquire signal from the digital to analog converter for transmitting, receive signals and transmit the same to the analog to digital converter for conversion.

The measuring frame 303 is made of a corrosion-resistant metal hard material for connecting N transceiver arrays and N reflectors, and a sliding structure is used between the upper and lower parts of the measuring frame to adjust the relative distances between the transceiving arrays and the reflectors 304. The reflectors 304 are cuboid, and are located directly under the different transceiving arrays to ensure that the corresponding receiving transducers can receive reflected signals sufficiently. The upper surfaces of all the reflectors (i.e., the sides opposite to the corresponding transceiving arrays) are in the same horizontal plane. The reflectors are equivalent to the corresponding transmitting transducers 301 in size, and are made of a material such as metal that facilitates signal reflection. The signal transmitting or receiving surfaces of the transducers of all the transceiving arrays are located in the same horizontal plane, and the upper surfaces of all the reflectors 304 are also in the same horizontal plane, so all the transceiving arrays are equidistant from the corresponding reflectors 304 directly under the transceiving arrays. In the present example, the different receiving transducers 302 are equidistant from the transmitting transducer 301 in the same transceiving array, that is, the distances from the centers of the signal receiving surfaces of the different receiving transducers 302 to the center of the signal transmitting surface of the transmitting transducer 301 in the same transceiving array are equal, so the distances L that the signals pass in the same transceiving array are equal.

The output module is configured to display the results of estimation and analysis of the processing module, or output the detection results to a next processing system so that the system responds according to the detection results.

Figure 7:
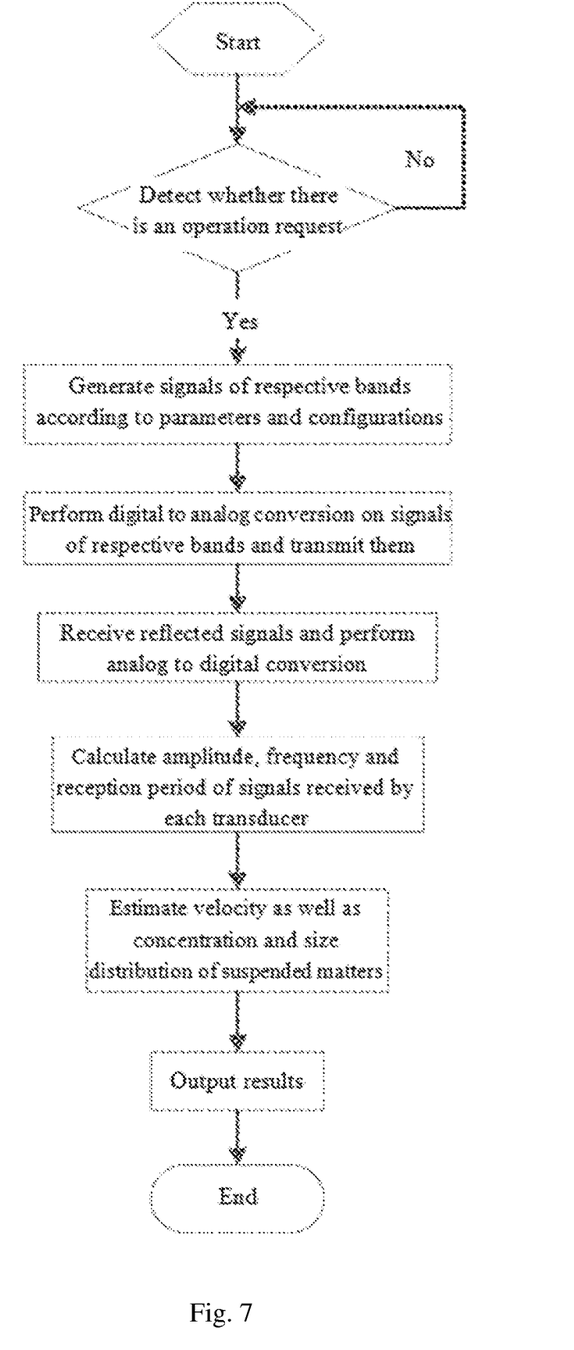
FIG. 7 is a flow diagram of a specific implementation process of the measuring device.

The operating steps of this device are shown in FIG. 7 as follows:

Step 1: according to the frequency range covered by each transducer in the array, signals of a corresponding center frequency are selected, and the amplitude and transmitting period thereof are determined. After operation parameters are input, the system detects whether the operation module has an operation request, and if there is an operation request, the processing module saves the parameters in response to the request.

Step 2: a measurement beginning signal is input through the operation module.

Step 3: upon receiving the measurement beginning signal, the processing module generates signals of respective bands according to the input parameters.

Step 4: the generated signals is transferred to the digital to analog converter to convert the same into analog signals, which is then transferred to the transceiving module, and the transceiving module transmits the signals through the transmitting transducers in the annular transceiving arrays of the corresponding frequency bands.

Step 5: the receiving transducers in each annular transceiving array receive reflected signals of the corresponding frequency bands, converts the same into electrical signals which then is transferred to the analog to digital converter.

Step 6: the digital signal processor first filters out the signals beyond the frequency ranges covered by each transducer, superimposes the filtered signals, calculates the amplitude, center frequency and receiving period or frequency of the power spectra of the received signals, and estimates the concentration, size and velocity of the suspended matters by using existing methods or formulas according to the specific description of the method in Example 1.

Step 8: the monitoring results (including size and corresponding concentration, and flow velocity of the water body with suspended matters) of the suspended matters is transferred to the output module which then outputs the results.

The above embodiments are preferred embodiments of the present invention, but the embodiments of the present inventions are not limited by the foregoing embodiments. Any other changes, modifications, substitutions, combinations or simplifications made without departing from the essence and principle of the present invention shall be considered as equivalent replacements, and shall be included within the protection scope of the present invention.

The invention claimed is:

1. A method for dynamically monitoring suspended matters based on an annular interleaving array, comprising the following steps:

S1 transmitting a signal;

wherein a measuring device is stationary relative to the ground and transmits the signal s(t) vertically downward in water containing suspended matters:

$$s(t) = A\frac{\sin(Wt)}{\pi t}\cos(2\pi f_0 t)$$

in the formula, A is the amplitude of the signal, W is the unilateral bandwidth of the signal, $f_0$ is the center frequency of the signal, and the power spectrum of the signal is a rectangular pulse having an amplitude of 0.5A, a bandwidth of 2W and a center frequency of $f_0$ on the positive axis:

$$S(f)=1/2A, f_0-W<f<f_0+W$$

the signal is transmitted once every period T, i.e., the transmission frequency is F=1/T, and the transmission duration is $T_0$, $T_0$<T;

the frequency range of s(t) is within frequency ranges of used transmitting transducer and receiving transducers, and a reflector is arranged directly under each transmitting transducer to ensure that the receiving transducers can receive reflected signals sufficiently;

S2 calculating the frequency of the signal arriving at the reflector;

wherein a 3D Cartesian coordinate system is established using the ground as the reference frame, the position of an ultrasonic transmitting probe S as the coordinate origin and the direction perpendicularly downward to the ground as the z direction, such that the coordinates of S are (0,0,0), the coordinates of the reflector G are (0,0,z), and a plurality of the receiving transducers and the ultrasonic transmitting probe S are in the same plane;

the transmitting transducer S transmits the signal in the positive direction of the z axis, namely $\overrightarrow{SG}$ direction, with a frequency F, and the unit vector in the z direction is expressed as $\vec{1}_{SG}$=(0,0,1); suppose the water velocity is $\vec{v}_w$=($v_{wx}$, $v_{wy}$, $v_{wz}$), wherein $v_{wx}$, $v_{wy}$ and $v_{wz}$ respectively represent components of the water velocity on coordinate axes x, y and z, then the water velocity in the S→G direction is:

$$v_{w\_SG}=\vec{v}_w \cdot \vec{1}_{SG}=v_{wz}$$

with small volume and mass, the suspended matters have a flow velocity in water mainly related to the water velocity, so the estimation of sedimentation velocity or flow velocity of the suspended matters can be converted into the calculation of flow velocity of the water body with suspended matters; assume that the propagation velocity of sound wave in water is c, since the signal transmitting point S is stationary, according to the Doppler effect, the frequency of the signal arriving at the reflector is:

$$f_G = \frac{c+v_{wz}}{c}F;$$

S3 calculating the frequency of the signal arriving at a receiving probe;

L represents the distance of transmitting the signal from the transmitting transducer S to the reflector G and finally to a receiving transducer $R_i$, $\overrightarrow{GR_i}$ is the propagation direction of the signal transmitted from the reflector G to the receiving transducer $R_i$, $\alpha_i$, $\beta_i$ and $\gamma_i$ are respectively angles between the vector $\overrightarrow{GR_i}$ and the coordinate axes x, y and z; the unit vector of the vector $\overrightarrow{GR_i}$, $\overrightarrow{1_{GR_i}} = (\cos \alpha_i, \cos \beta_i, \cos \gamma_i)$, is thus obtained, and the water velocity in the G→$R_i$ direction is:

$$v_{w\_GR_i} = \overrightarrow{v_w} \cdot \overrightarrow{1_{GR_i}} = v_{wx} \cos \alpha_i + v_{wy} \cos \beta_i + v_{wz} \cos \gamma_i;$$

when the sound wave is propagated from the reflector G to the receiving point $R_i$, the signal is subject to the Doppler effect under the action of water flow; the signal s(t) is transmitted once every period T at the transmission terminal, and is subject to the Doppler shift due to the Doppler effect in the process of propagation in water, so the reflected signal $r_i(t)$ finally received by the receiving terminal $R_i$ has a period of $T_{R_i}$, and a receiving frequency of $f_{R_i} = 1/T_{R_i}$; since the receiving terminal does not move, the frequency of the signal arriving at the $i^{th}$ receiving transducer $R_i$ is:

$$f_{R_i} = \frac{c}{c + v_{w\_GR_i}} f_G;$$

after rearrangement, in a process from transmitting to receiving the signal s(t), the relationship between the receiving frequency and the transmitting frequency is:

$$\begin{aligned} f_{R_i} &= \frac{c + v_{wx}}{c} \cdot \frac{c}{c + v_{w\_GR_i}} F \\ &= \frac{c + v_{wx}}{c + v_{wx}\cos\alpha_i + v_{wy}\cos\beta_i + v_{wz}\cos\gamma_i} F \\ &= (1 + \Delta_i)F \end{aligned}$$

wherein $\Delta$ is a Doppler factor;

S4 providing M (M≥3) receiving transducers to list M equations shown above to obtain the three unknown numbers, thus obtaining a three-dimensional flow velocity of the water body with suspended matters, i.e., the velocity of the suspended matters; one transmitting transducer and M receiving transducers form one transceiver array;

S5 estimating the concentration and size distribution of the suspended matters;

wherein the process of estimating the concentration and size distribution of the suspended matters by signal power spectra is as follows:

S5-1 sampling;

since the signal s(t) is attenuated in water and affected by the Doppler effect, the signal sampled from $r_i(t)$ (i=1, 2, . . . , M) received by the $i^{th}$ receiving transducer $R_i$ is:

$$r_i(n) = B_i \frac{\sin[(1+\Delta_i)WnT_s]}{\pi(1+\Delta_i)nT_s} \cos[2\pi(1+\Delta_i)f_0 nT_s] + w_i(n)$$

wherein $B_i$ and $\Delta_i$ are respectively the amplitude and the Doppler factor of the received signal, $w_i(n)$ is signal noise, the sampling frequency is $f_s = 1/T_s$ ($f_s > 2f(f_0+W)$), and $\Delta_i$ can be obtained from step S3;

S5-2 performing 2N point discrete Fourier transform to obtain $r_i(n)$ $$S_{R_i}(k) = \sum_{n=0}^{N-1} R_i(n) e^{-j\frac{2\pi}{N}nk}, 0 \le k \le N-1$$

wherein $R_i(n)$ is the autocorrelation function of the received signal; $r_i(n)$ S5-3 analyzing the signal of the transceiving array, wherein the system function of the transmitting transducer S is $H_1(f)$, the system functions of the receiving transducers are all $H_2(f)$, the receiving transducers in a same transceiving array have the same parameters, and the system functions $H_1(f)$ and $H_2(f)$ can be obtained by checking the corresponding transducer parameters;

the signal s(t) is transmitted after passing through the system $H_1(f)$, and the received signal $r_i(t)$ also passes through the system $H_2(f)$, so the signal power spectra before and after propagation in water are respectively $H_1(f)S(f)$ and $S_{R_i}(f)/H_2(f)$;

S5-4 from step S5-3, the discrete signal power spectrum of the signal at the corresponding frequency $f_s k/N$ of the receiving transducer $R_i$ is $$\frac{S_{R_i}(k)}{H_2(f_s k/N)},$$

and the discrete signal power spectrum of the signal at the corresponding frequency $f_s k/N$ of the transmitting transducer S is $$\frac{A}{2} H_1(f_s k/N),$$

then an attenuation parameter $Q_k$ is obtained:

$$Q_k = \frac{\sum_{i=1}^{3} \frac{S_{R_i}(k)}{H_2(f_s k/N)}}{\frac{A}{2} H_1(f_s k/N)}, k = 0, 1, \ldots, N-1;$$

which indicates the attenuation parameter of the signal before and after passing through the water body;

S5-5 for the signals received by M receiving transducers, superimposing discrete power spectra of corresponding intervals of the signals, and obtaining the concentration of the suspended matters according to the attenuation parameter $Q_k$ (k=0,1, . . . , N-1) and the transmission distance L, wherein each frequency $f_s k/N$ of the signal corresponds to the concentration of the suspended matters with a size of quarter-wavelength.

2. The method for dynamically monitoring suspended matters as claimed in claim 1, wherein a plurality of transmitting transducers are used; each transmitting transducer transmits signals of a different frequency range; if a wide frequency range to be measured is [$f_1$, $f_m$], the wide frequency band may be divided into N bands: [$f_1$, $f_2$], [$f_3$, $f_4$], . . . , [$f_{m-1}$, $f_m$], N transmitting transducers are used, where a first transducer transmits signal $s_1(t)$ in a frequency range [$f_1$, $f_2$], a second transducer transmits signal $s_2(t)$ in a frequency range [$f_3$, $f_4$], and so on; one transmitting transducer corresponds to one transceiving array, and steps S1-S5 are repeated for different transceiving arrays to estimate the concentration, size distribution and velocity of the suspended matters in the water body.

3. The method for dynamically monitoring suspended matters as claimed in claim 1, wherein different frequency bands are consecutive or separated by a certain interval.

4. A monitoring device for performing the method of claim 1, comprising an operation module, a processing module, a transceiving module, an output module and a power supply, wherein the power supply supplies power to all the modules; the operation module is connected with the processing module, and the processing module is connected with the transceiving module and the output module respectively;

the transceiving module comprises a measuring frame, N reflectors and N transceiving arrays; the measuring frame is used for connecting and fixing the reflectors and different transceiving arrays; the transceiving arrays are separated by a certain distance; each transceiving array comprises a transmitting transducer and M ($M \geq 3$) receiving transducers, and signal transmitting or receiving surfaces of all the transducers are in the same horizontal plane; the receiving transducers in each transceiving array are connected to the transmitting transducer, distances between the receiving transducers and the transmitting transducer in the same transceiving array are the same, and frequencies of the transmitting and receiving transducers in the same transceiving array are matched; the reflectors are located directly under the different transceiving arrays, and reflecting surfaces of the N reflectors are in the same horizontal plane;

when an operator inputs corresponding parameters to the operation module, the processing module generates signals of respective bands according to the parameter, transfers the signals to the transmitting transducers of the transceiving arrays with corresponding frequency bands in the transceiving module for transmission, and controls transmission periods of the transmitting transducers; for the signals transmitted by the transmitting transducer in a transceiving array, the corresponding receiving transducer array receives the reflected signals and transfers the reflected signals to the processing module; the processing module calculates the concentration and size distribution of the suspended matters, and calculates the three-dimensional flow velocity of water body with the suspended matters according to the Doppler effect; finally the measured concentration and size distribution of the suspended matters and the flow velocity of the water body are transferred to the output module for output display.

5. The monitoring device as claimed in claim 4, wherein the amount N of the transceiving arrays depends on the application scenario and range of measurement.

6. The monitoring device as claimed in claim 4, wherein a crossarm of the measuring frame for fixing the reflectors can be adjusted up and down to modify the height thereof.

7. The monitoring device as claimed in claim 4, wherein the processing module comprises a digital processor, a digital to analog converter and an analog to digital converter.

8. The monitoring device as claimed in claim 4, wherein the reflectors are made of a material that facilitates signal reflection.

9. The monitoring device as claimed in claim 4, wherein the measuring frame is made of a corrosion-resistant hard material.

10. The monitoring device as claimed in claim 4, wherein the transceiving arrays are connected by a metal or plastic material.

* * * * *